(12) United States Patent
Ito et al.

(10) Patent No.: US 9,366,625 B2
(45) Date of Patent: Jun. 14, 2016

(54) SURFACE MEASUREMENT DEVICE

(71) Applicant: Hitachi High-Technologies Corporation, Minato-ku, Tokyo (JP)

(72) Inventors: Masaaki Ito, Tokyo (JP); Takahiro Jingu, Tokyo (JP); Takanori Kondo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/376,479

(22) PCT Filed: Jan. 16, 2013

(86) PCT No.: PCT/JP2013/050618
§ 371 (c)(1),
(2) Date: Aug. 4, 2014

(87) PCT Pub. No.: WO2013/118543
PCT Pub. Date: Aug. 15, 2013

(65) Prior Publication Data
US 2014/0375988 A1 Dec. 25, 2014

(30) Foreign Application Priority Data

Feb. 9, 2012 (JP) .................................. 2012-025678

(51) Int. Cl.
*G01B 11/30* (2006.01)
*G01N 21/55* (2014.01)
(Continued)

(52) U.S. Cl.
CPC .............. *G01N 21/55* (2013.01); *G01B 11/303* (2013.01); *G01N 21/9501* (2013.01); *G01N 33/00* (2013.01); *G01N 2033/0095* (2013.01); *H01L 22/12* (2013.01)

(58) Field of Classification Search
CPC ..... G01N 21/55; G01N 21/9501; G01N 33/00; G01B 11/303
USPC .................................................. 356/600–640
See application file for complete search history.

(56) References Cited

U.S. PATENT DOCUMENTS

| 5,428,442 A | 6/1995 | Lin et al. |
| 7,286,218 B2 | 10/2007 | Tiemeyer et al. |

(Continued)

FOREIGN PATENT DOCUMENTS

| JP | 07-333164 A | 12/1995 |
| JP | 09-503299 A | 3/1997 |

(Continued)

*Primary Examiner* — Kara E Geisel
*Assistant Examiner* — Hina F Ayub
(74) *Attorney, Agent, or Firm* — Miles & Strockbridge P.C.

(57) ABSTRACT

In conventional technologies in surface measurement and defect inspection, considerations are not made for the following points: (1) coarseness of resolution of spatial frequency; (2) variation of detection signal resulting from anisotropy of microroughness; and (3) variation of background signal resulting from anisotropy of microroughness. The present invention is characterized by acquiring a feature quantity about the anisotropy of the microroughness of the substrate surface. Further, the present invention is characterized by acquiring a surface state in consideration of the anisotropy of the microroughness of the substrate surface. Further the present invention is characterized by detecting a defect over the substrate in consideration of the anisotropy of the microroughness of the substrate surface.

13 Claims, 10 Drawing Sheets

(51) Int. Cl.
*G01N 21/95* (2006.01)
*G01N 33/00* (2006.01)
*H01L 21/66* (2006.01)

(56) References Cited

U.S. PATENT DOCUMENTS

| | | | |
|---|---|---|---|
| 8,101,935 B2 | 1/2012 | Takahashi et al. | |
| 2003/0016366 A1* | 1/2003 | Takeda | G06T 7/0057 356/604 |
| 2006/0181700 A1* | 8/2006 | Andrews | G01N 21/21 356/237.2 |
| 2009/0290168 A1* | 11/2009 | Hamamatsu | G01B 11/303 356/600 |

FOREIGN PATENT DOCUMENTS

| | | |
|---|---|---|
| JP | 2000-031224 A | 1/2000 |
| JP | 2006-278515 A | 10/2006 |
| JP | 2007-500881 A | 1/2007 |
| JP | 2007-501944 A | 2/2007 |
| JP | 2008-278515 A | 11/2008 |
| JP | 2010-223770 A | 10/2010 |

* cited by examiner (a) DIRECTION OF LARGE ROUGHNESS (b) DIRECTION OF SMALL ROUGHNESS (a) CHIEF AXIS DIRECTION = 0°
(b) CHIEF AXIS DIRECTION = 30°
(c) CHIEF AXIS DIRECTION = 60°
(d) CHIEF AXIS DIRECTION = 90°

(a) SMALL ELLIPTICITY
(b) LARGE ELLIPTICITY (a) LOW SPATIAL FREQUENCY COMPONENT IS LARGE (b) HIGH SPATIAL FREQUENCY COMPONENT IS LARGE (a) ANISOTROPY OF POWER
(INDICATED BY SHADES OF GRAY)

(b) SPATIAL FREQUENCY CHARACTERISTIC

— WAFER EDGE

SURFACE MEASUREMENT DEVICE

TECHNICAL FIELD

The present invention relates to a surface measurement device for measuring roughness of a substrate surface, and an inspection device for inspecting defects of the substrate surface. For example, the present invention relates to surface measurement and inspection device using a light scattering method, and especially relates to microroughness measurement and defect inspection over a wafer surface etc. in a semiconductor device manufacturing process.

BACKGROUND ART

In connection with miniaturization of semiconductor devices, microroughness of surfaces of a bare wafer and a film-coated wafer has come to have a large influence on their electrical characteristics. Since the microroughness occurs in processes such as polishing, cleaning, deposition, thermal process, and planarization, in order to make the device have high performance and improve a yield thereof, it is necessary to measure the microroughness for every process and manage a state and process conditions of a process apparatus properly.

Since an amplitude of the microroughness is very small, ranging from a subnanometer to a nanometer, its 3-D shape is measured using an atomic force microscope (AFM). However, since the measurement by the AFM requires a long time, in-line measurement of an entire surface of the wafer is substantially impossible.

On the other hand, it is known conventionally that the microroughness has correlation with light scattering. A microroughness measurement device using the light scattering method is disclosed, for example, in the U.S. Pat. No. 7,286,218 (Patent Literature 5). As other advanced technologies, Patent Literatures 1 through 4, 6, and 7 are enumerated.

Moreover, in connection with the miniaturization of the semiconductor devices, improvement of detection sensitivity for defects of a minute particle, a bump, a scratch, etc. is required over the surface of the bare wafer or the film-coated wafer.

In order to improve sensitivity of the surface inspection device using the light scattering method, it is necessary to increase a detection signal of the scattered light from a defect (a defect signal) and to reduce a detection signal of the scattered light from the microroughness (a background signal). Regarding the reduction of the background signal, filtering by signal processing is disclosed, for example, in the Japanese Unexamined Patent Application Publication No. 2007-501944 (Patent Literature 8).

CITATION LIST

Patent Literature

Patent Literature 1: Japanese Unexamined Patent Application Publication No. Hei9(1997)-503299
Patent Literature 2: Japanese Unexamined Patent Application Publication No. Hei7(1995)-333164
Patent Literature 3: Japanese Unexamined Patent Application Publication No. 2010-223770
Patent Literature 4: Japanese Unexamined Patent Application Publication (Translation of PCT Application) No. 2007-500881
Patent Literature 5: U.S. Pat. No. 7,286,218
Patent Literature 6: U.S. Pat. No. 5,428,442
Patent Literature 7: Japanese Unexamined Patent Application Publication No. 2008-278515
Patent Literature 8: Japanese Unexamined Patent Application Publication (Translation of PCT Application) No. 2007-501944

SUMMARY OF INVENTION

Technical Problem

In Patent Literature 5, it is said that apertures of multiple detection optical systems are associated with the spatial frequency ranges of microroughness, and a root-mean-square (RMS) can be evaluated for every spatial frequency range. However, since the number of divisions of the spatial frequency range is the same as the number of detection optical systems (in this embodiment, six), a point that a resolution of spatial frequency is coarse has not been taken into account.

Moreover, although a spatial distribution of the scattered light varies in various directions, to the front, the back, and the side, according to a difference in the microroughness, a variation of the scattered light that does not enter into the aperture of the detection optical system has not been taken into account.

Moreover, it is known conventionally that there is a step-terrace structure in a specific direction and in a specific spatial frequency over a surface of an epitaxial growth wafer (hereinafter, called an epitaxial wafer). In the present invention, the inventors have found that about the microroughness of the epitaxial wafer, anisotropy in a wide spatial frequency range exists besides the step-terrace structure. Then, the inventors have found that because of this anisotropy, even with the same microroughness, the spatial distribution of the scattered light may vary according to an azimuth of illumination light. A variation of the detection signal resulting from such anisotropy of the microroughness was not taken into account in the conventional technologies.

Moreover, in Patent Literature 8, it is supposed that low spatial frequency components of a background signal can be reduced. However, an optical change of the background signal resulting from the anisotropy of the microroughness like that of the epitaxial wafer was not taken into account.

Organizing problems that the conventional technologies did not take into account, they can be expressed as follows, for example.

(1) Coarseness of resolution of spatial frequency
(2) Variation of detection signal resulting from anisotropy of microroughness
(3) Variation of background signal resulting from anisotropy of microroughness.

The present invention solves at least one of the problems (1) to (3) described above, for example. Then, the first object of the present invention is to provide a surface measurement device capable of high precision measurement of surface roughness in microroughness having anisotropy and its method. Moreover, the second object of the present invention is to provide a surface inspection device capable of high-sensitivity detection of a defect in a surface with the microroughness having anisotropy and its method.

Solution to Problem

The present invention is characterized by acquiring a feature quantity about the anisotropy of the microroughness of the substrate surface.

The present invention is characterized by acquiring a surface state in consideration of the anisotropy of the microroughness of the substrate surface.

The present invention is characterized by detecting a surface defect in consideration of the anisotropy of the microroughness of the substrate surface.

Explaining more concretely, it can also be expressed as follows, for example. The present invention is characterized by continuously acquiring the 2-D spatial frequency spectrum that is defined by the mutually orthogonal spatial frequency axes regarding the surface roughness.

In the surface measurement device that illuminates light onto a sample surface, detects scattered light from the sample surface with the multiple detection optical systems, and measures roughness of the sample surface from the multiple detection signals, the present invention is characterized in that directions of optical axes of the detection optical systems are mutually different, and the device includes processing of computing a 2-D spatial frequency spectrum of the sample surface.

The present invention is characterized by that the illumination light is a spot beam and the illumination light scans the sample surface by rotation and linear motion of the sample.

The present invention is characterized in that optical axes of at least the two detection optical systems lie in a plane perpendicular to a plane of incidence of the sample and apertures are symmetrical relative to the plane of incidence.

The present invention is characterized in that optical axes of at least the two detection optical systems lie in a plane perpendicular to the plane the incidence of the sample, apertures are symmetrical relative to the plane of incidence, and optical axes of at least the two detection optical systems lie in a plane parallel to the plane of incidence.

The present invention is characterized by including processing of recording in advance a relationship between the 2-D spatial frequency spectrum of known surface roughness and the detection signal in a library, comparing the detection signal from the sample surface with the library, and computing the 2-D spatial frequency spectrum of the sample surface.

The present invention is characterized by including processing of calculating a sum total of the multiple detection signals, and processing of calculating ratios (detection signal ratios) of respective detection signals and the detection signal sum total.

The present invention is characterized by including processing of computing a predetermined feature quantity of the sample surface using the 2-D spatial frequency spectrum, and outputting a map of the feature quantity of the whole of the sample surface or a predetermined range thereof.

The present invention is characterized in that the feature quantity is at least a chief-axis angle of the anisotropy of the 2-D spatial frequency spectrum, or ellipticity of the anisotropy, or RMS roughness in a predetermined 2-D spatial frequency range, or a cutoff spatial frequency of the 2-D spatial frequency spectrum, or a peak spatial frequency, or a thickness of a film that forms the sample surface.

The present invention is characterized by including processing of computing a 3-D shape of the sample surface using the 2-D spatial frequency spectrum at a predetermined position of the sample surface, and by outputting the 3-D shape.

In a surface measurement method whereby light is illuminated onto the sample surface, the scattered light from the sample surface is detected by the multiple detection optical systems, and the roughness of the sample surface is measured from the multiple detection signals, the present invention is characterized in that directions of the optical axes of the detection optical systems are mutually different and the method includes processing of computing the 2-D spatial frequency spectrum of the sample surface.

In the surface inspection device that illuminates light onto the sample surface, and detects the scattered light from the sample surface with the multiple detection optical systems, and detects the defect of the sample surface by processing the multiple detection signals, the present invention is characterized by including a step of multiplying the multiple detection signals by weight coefficients and a step of acquiring the signal sum total by adding outputs of the above-mentioned step, and in that the weight coefficients are a function of an argument in a polar coordinate system of the sample surface.

Advantageous Effects of Invention

The present invention creates at least one of the following effects:

(1) A detailed state of the substrate surface can be acquired. Expressing this effect more intelligibly, it can also be expressed that high precision measurement of the microroughness having anisotropy becomes possible, for example, by detecting the spatial distribution of the scattered light and computing the 2-D spatial frequency spectrum.

(2) High-sensitivity detection of a defect becomes possible. Expressing this effect more intelligibly, it can also be expressed that high-sensitivity detection of a defect becomes possible over a surface with the microroughness having anisotropy, for example, by multiplying the detection signal by a weight according to an argument of an inspection position over the wafer.

DESCRIPTION OF EMBODIMENTS

Hereafter, embodiments will be described using drawings.

First Embodiment

Figure 1:
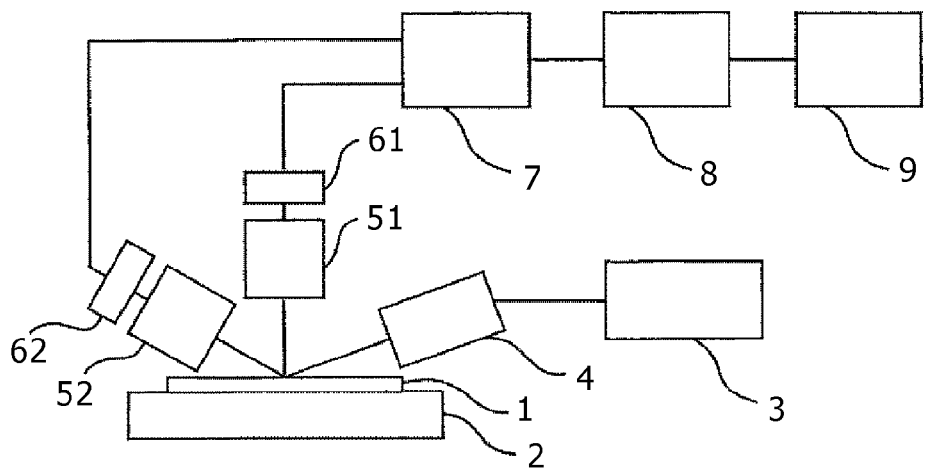
FIG. 1 is a diagram showing an outline configuration of a surface measurement device according to the present invention.

As one embodiment of the present invention, a measurement device of microroughness of a wafer surface in semiconductor device manufacture will be explained. FIG. 1 shows an outline configuration of the surface measurement device. Its main components are a stage 2 that mounts thereon a wafer 1, a light source 3, an illumination optical system 4 having lenses, mirrors, etc., detection optical systems 51 to 59 (53 to 59 are not illustrated) that have lenses, mirrors, etc., photodetectors 61 to 69 (63 to 69 are not illustrated) for detecting light that is collected by the detection optical systems 51 to 59, a signal processing system 7, a control system 8, and an operation system 9. Incidentally, the detection optical systems 51 to 59 are arranged so that at least one of an elevation angle and an azimuth angle to the wafer 1 may be different. In connection with it, the photodetectors 61 to 69 are also arranged so that at least one of the elevation angle and the azimuth angle to the wafer 1 may be different.

Figure 2:
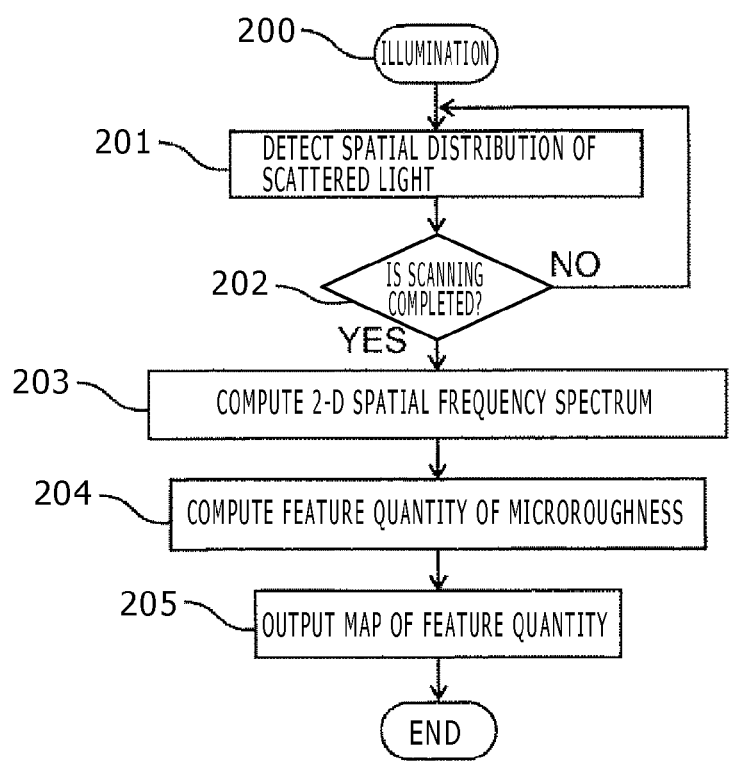
FIG. 2 is a diagram showing a flow of surface measurement according to the present invention.

Next, a flow of surface measurement in this embodiment will be explained using FIG. 2. Light of a predetermined wavelength emitted from the light source 3 is made into a predetermined polarization by a polarization filter (not illustrated). The light from the light source 3 passes through the illumination optical system 4 containing lenses, mirrors, etc. Then, the light that passed through the illumination optical system 4 illuminates the wafer 1 at a predetermined incident angle and at a predetermined azimuth (projection to the wafer surface in a direction of illumination light), and, as a result, a spot beam of a predetermined size is formed over the wafer 1. The azimuth of the illumination light and a spot beam position over the wafer are fixed. The azimuth of the illumination light is parallel, for example, to a straight line that connects the spot beam position and a wafer center. The operation explained heretofore is expressed as Step 200 of FIG. 2.

By the illumination of the spot beam, the scattered light by the microroughness of the surface of the wafer 1 diverges. The scattered light is collected by the detection optical systems 51 to 59, and is detected by the photodetectors 61 to 69. This operation is included in Step 201 of FIG. 2.

Figure 3:
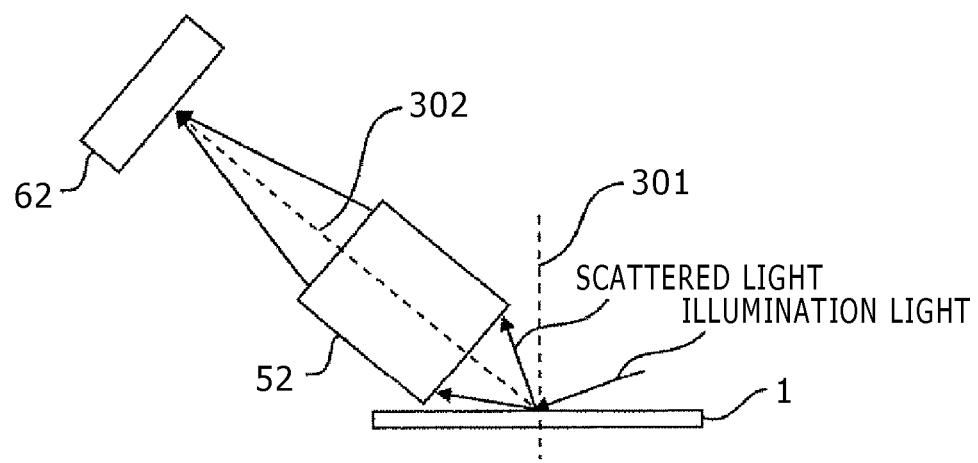
FIG. 3 is a diagram showing a set of a detection optical system and a photodetector in a first embodiment of the surface measurement device according to the present invention.

Here, a collecting operation that the detection optical systems 51 to 59 perform will be explained. FIG. 3 shows scattered light detection by a set of a detection optical system and a photodetector. In this embodiment, the detection optical system 52 and the photodetector 62 are arranged so that specular reflection light from the surface of the wafer 1 may not be detected. That is, a dark field image of the spot beam over the wafer 1 will be imaged. As described above, since the detection optical systems 51 to 59 are arranged so that at least one of the elevation angle and the azimuth angle to the wafer 1 may differ, that is, directions of optical axes of the detection optical systems 51 to 59 are mutually different, a set of the detection signals will reflect a spatial distribution of the scattered light (hereinafter, called a scattered light distribution). This indicates that the surface measurement device of this embodiment can acquire the scattered light distribution from the microroughness (Step 201 of FIG. 2).

The detected signal is converted into a digital signal by an AD converter (not illustrated), and is transmitted to the signal processing system 7. The control system 8 moves the stage 2 so that the spot beam may scan an entire surface of the wafer or a predetermined range thereof while acquiring the detection signal. The stage 2 is such that a rotary stage is mounted over a linear motion stage.

Figure 4:
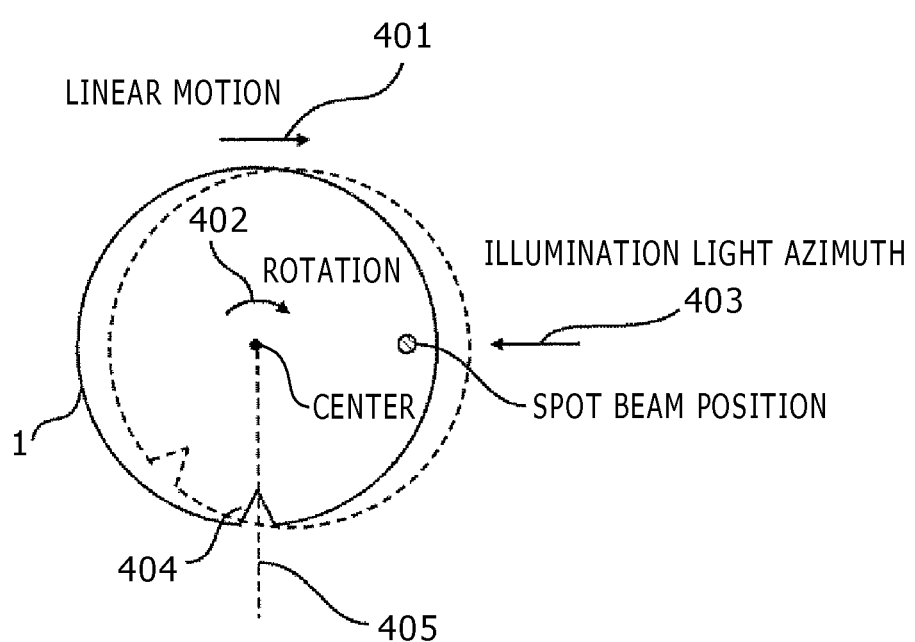
FIG. 4 is a diagram showing rotation and linear motion of a wafer.

Here, a scanning operation performed between the spot beam and the wafer 1 will be explained. In this embodiment, as shown in FIG. 4, the wafer 1 performs linear motion in a direction of an arrow 401 (this can be expressed as a substantially parallel direction to the azimuth of the illumination light) by the stage 2 and rotates in a direction of an arrow 402. Therefore, a locus of the spot beam over the wafer 1 becomes spiral. The signal processing system 7 memorizes a measurement position over the wafer 1 by a polar coordinate system (a coordinate system expressing a position with a radius and an argument) that designates the center of the wafer 1 to be an origin. The argument varies according to rotation of the wafer 1, and can be expressed on the basis of a reference line 405 (for example, a half line passing through a notch 404 and the wafer center) presupposed over the wafer. The position coordinates and the detection signal over the wafer 1 will be accumulated one by one in the signal processing system 7 by the above scanning operation. This operation is included in Step 202 of FIG. 2.

Then, after completion of the scanning of the entire surface of the wafer 1 or the predetermined range thereof (Step 202), the signal processing system 7 performs subsequent processing. There is a storage medium that saves a library in the inside of the signal processing system 7, and in this library, a relationship between the 2-D spatial frequency spectrum and the detection signal under optical conditions at the time of acquiring the scattered light distribution about a large number of known microroughnesses is recorded. The signal processing system 7 acquires the 2-D spatial frequency spectrum by referring to the detected scattered light distribution and data in this library. More specifically, the signal processing system 7 compares the detected detection signal and a detection signal in the library, and acquires the 2-D spatial frequency spectrum of the most analogous detection signal (Step 203).

Figure 11:
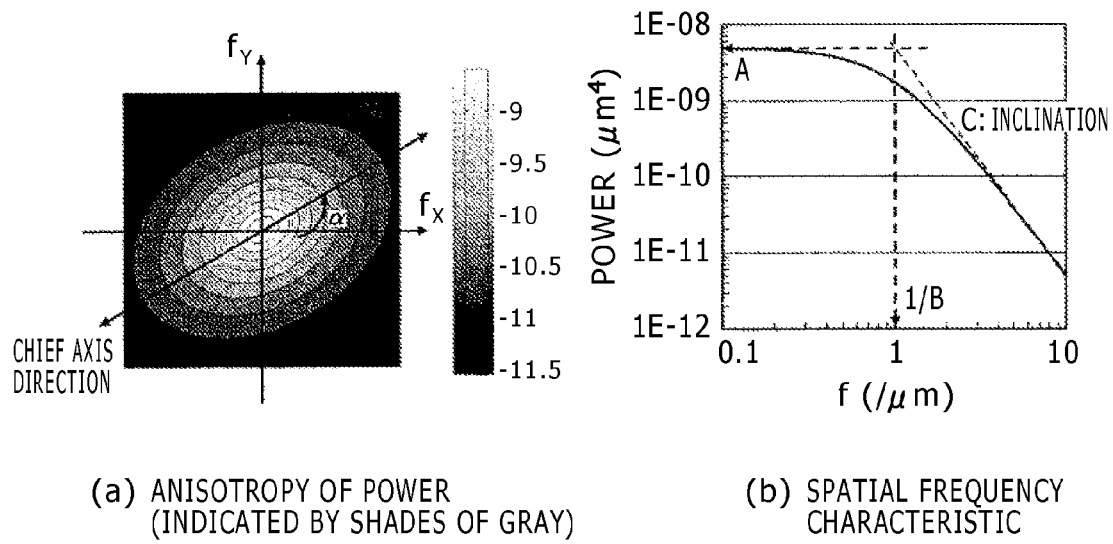
FIG. 11 is a diagram showing one example of the 2-D spatial frequency spectrum expressed with an anisotropic ABC-type function.

Here, the 2-D frequency spectrum will be explained. The 2-D spatial frequency spectrum can be expressed as a power acquired, when the surface shape is expressed by 3-D coordinates (X, Y, Z), by 2-D Fourier transforming a height Z with respect to (X, Y) and squaring an absolute value of the amplitude. That is, the 2-D spatial frequency spectrum is defined by two spatial frequency axes of an X-direction and a Y-direction that intersect (specifically, intersecting orthogonally). Incidentally, although details of the 2-D spatial frequency spectrum will be described later, the 2-D spatial frequency spectrum acquired in this embodiment becomes continuous in 2-D spatial frequency axes as shown in FIG. 11.

Next, after acquiring the 2-D spatial frequency spectrum, the signal processing system 7 computes the feature quantity of the microroughness using the 2-D spatial frequency spectrum (Step 204), and transmits it to the control system 8. Incidentally, details of the feature quantity will be described later. Then, after computing the feature quantity of the entire surface of the wafer or the predetermined range thereof, a map of the feature quantity is displayed in the operation system 9 (Step 205).

As the light source 3 of this embodiment, single wavelength light sources such as a laser and a light emitting diode of a visible light range, an ultraviolet light range, and a deep ultraviolet light range, and the like can be used. Moreover, continuous wavelength light sources such as a mercury lamp and a xenon lamp can also be used. In the case of the continuous wavelength light source, single wavelength light can be selected by a wavelength filter according to a sample surface.

Moreover, regarding polarization of the illumination light of the embodiment, s-polarized light, p-polarized light, circularly polarized light, elliptically polarized light, etc. can be selected according to the sample surface. Regarding a spot beam size of the illumination light, it can be selected according to a spatial resolution necessary at the measurement position. Regarding an incident angle of the illumination light, it can be selected from grazing incidence to normal incidence according to the sample surface.

Moreover, as the illumination optical system 4 and the detection optical systems 51 to 59 of the embodiment, a refractive type comprised of lenses, a reflective type comprised of mirrors, a catadioptric type that combines mirrors and lenses, a diffraction type such as a Fresnel zone plate can be used.

Moreover, as the photodetectors 61 to 69 of the embodiment, a photomultiplier tube, a multi-pixel photon counter, an avalanche photodiode array, etc. can be used.

Moreover, the library of the embodiment can be created using a test wafer. The test wafer is one that is manufactured with the process conditions changed intentionally in processes such as polishing, cleaning, deposition, thermal process, planarization, etc. The microroughness is measured using an AFM at a sampling position over the surface of the test wafer and the 2-D spatial frequency spectrum is computed. Then, the test wafer is mounted over the surface measurement device of this embodiment and the detection signal is acquired at the sampling position. In this way, the relationship between the 2-D spatial frequency spectrum and the detection signal can be recorded for known microroughness.

Moreover, the library of the embodiment can also be created using numerical simulation. First, the 2-D spatial frequency spectrum corresponding to arbitrary microroughness is defined. Next, by using the 2-D spatial frequency spectrum, the complex refractive index and the film thickness of a surface material, and illumination conditions (for example, a wavelength, polarization, an incident angle, an azimuth angle, etc. of the illumination light) as input data, the scattered light distribution is calculated using a bidirectional reflectance distribution function (BRDF method) etc. Then, an intensity of the scattered light (being proportional to the detection signal) that the detection optical system collects is calculated using the calculated value of the scattered light distribution. Thus, by the numerical simulation, a relationship between a large number of the 2-D spatial frequency spectra and the detection signals can be recorded in the library even without using the test wafer.

Next, a mechanism whereby measurement accuracy of microroughness having anisotropy is improved by the surface measurement device of this embodiment will be explained.

Figure 5:
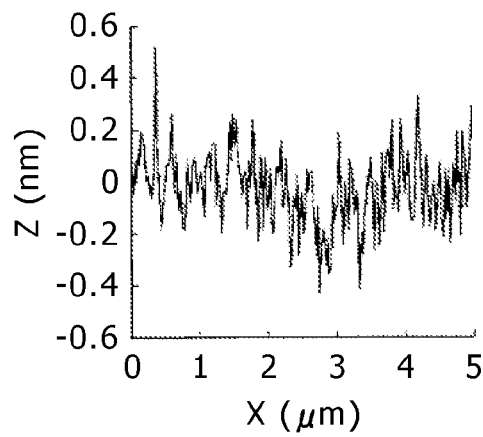
FIG. 5 is a diagram showing one example of an AFM measurement value of microroughness.
Figure 5:
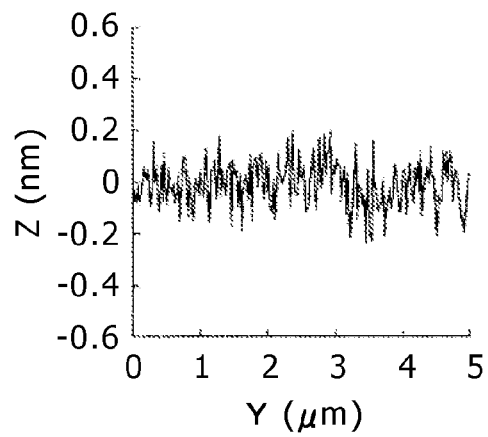

FIG. 5 shows one example of an AFM measurement value of the microroughness having anisotropy in a direction in which an amplitude of roughness is large, and in a direction in which it is small. FIG. 5 (a) represents the microroughness in a certain direction (here, being supposed as the X-direction, for convenience) over the substrate. FIG. 5 (b) represents the microroughness in a direction intersecting the X-direction (more specifically, intersecting orthogonally). F g. 5 represents that a state of FIG. 5 (a) is larger in roughness than a state of FIG. 5 (b). Thus, a degree by which microroughnesses differ with respect to two directions in a certain plane can be expressed as anisotropy of microroughness. Generally, the microroughness having anisotropy can be regarded as a set of roughnesses of various spatial frequencies in various directions. The 2-D spatial frequency spectrum expresses a quantity related to an amplitude of roughness in the 2-D spatial frequency axes.

In this embodiment, a direction in which the 2-D spatial frequency spectrum is a maximum is called a chief axis of the anisotropy in the following explanation. In many cases, the 2-D spatial frequency spectrum is a minimum in a direction orthogonal to the chief axis.

Moreover, denoting the maximum of the 2-D spatial frequency spectrum as $P_{max}$ and the minimum as $P_{min}$, "$1-(P_{min}/P_{max})$" is called ellipticity of the anisotropy in the following explanation. The ellipticity is not less than zero and not more than unity, and with a larger ellipticity, the anisotropy is more remarkable. That is, directions in which the 2-D spatial frequency spectrum is the maximum and the minimum can be known by acquiring a direction of the chief axis. Moreover, a degree of the anisotropy can be known by acquiring the ellipticity of the anisotropy.

Figure 6:
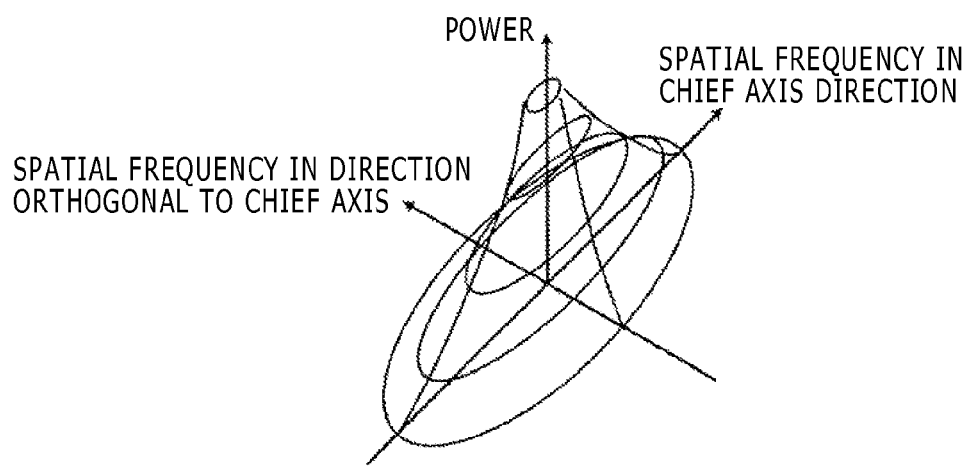
FIG. 6 is a diagram showing contour lines of a 2-D spatial frequency spectrum.

FIG. 6 shows the 2-D spatial frequency spectrum with contour lines for the microroughness having anisotropy. In the following, a relationship between the 2-D spatial frequency spectrum and the scattered light distribution will be explained for the microroughness having anisotropy. In this embodiment, as described above, the wafer 1 is rotated by the stage 2, while the wafer 1 is illuminated from one direction. Therefore, a chief axis direction of the anisotropy varies to the azimuth of the illumination light with the rotation of the wafer 1.

Figure 7:
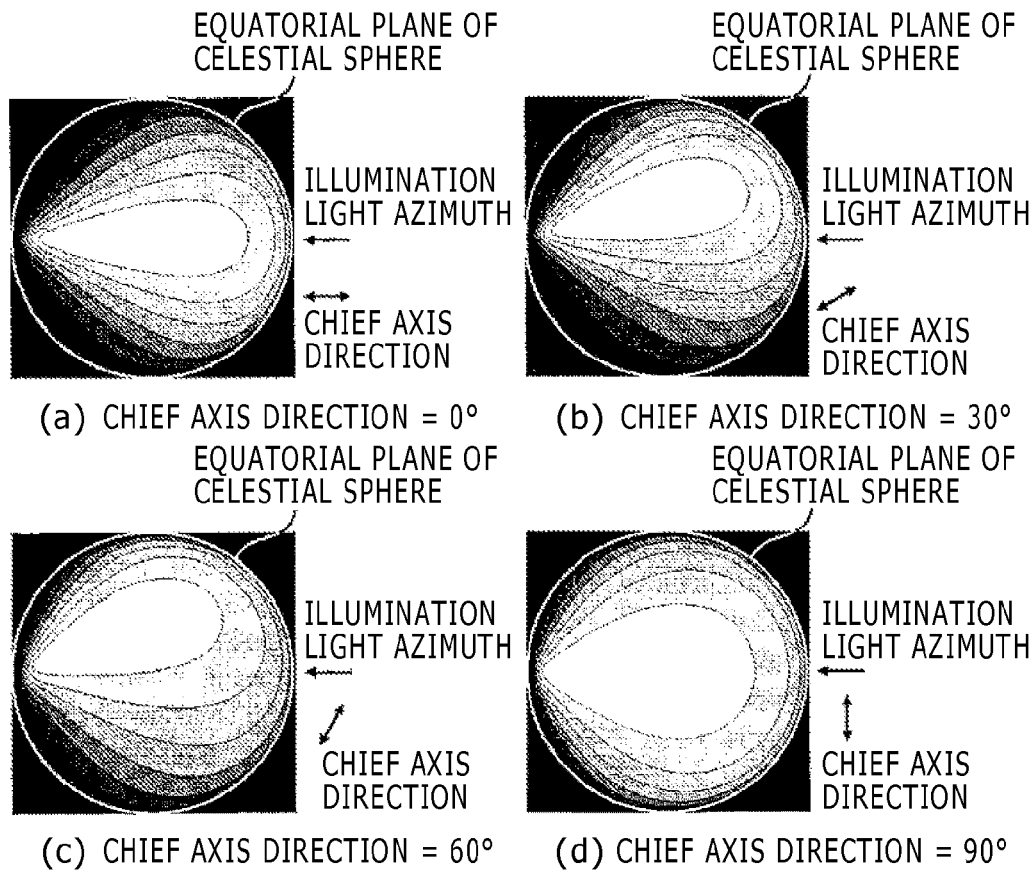
FIG. 7 is a diagram explaining a relationship between a chief axis direction of the anisotropy and a scattered light distribution.

FIG. 7 shows a relationship between the chief axis direction of the anisotropy and the scattered light distribution. A display method of the scattered light distribution is to project the intensity distribution on a celestial sphere onto a plane parallel to the wafer surface, and it is shown that the brighter the gray image, the larger the intensity becomes. It turns out that the scattered light distribution varies according to the chief axis direction of the anisotropy. For example, defining a plane that contains a direction of the illumination light and a normal of the wafer surface as a plane of incidence, when comparing a state of FIG. 7 (a) (a state where the plane of incidence and the chief axis direction are parallel) and states of FIGS. 7 (b), (c), and (d), the intensity distribution of the scattered light varies largely especially in a direction perpendicular to the plane of incidence. Moreover, when the chief axis of the anisotropy is parallel or perpendicular to the azimuth of the illumination light, the scattered light distribution becomes symmetrical relative to the plane of incidence.

Figure 8:
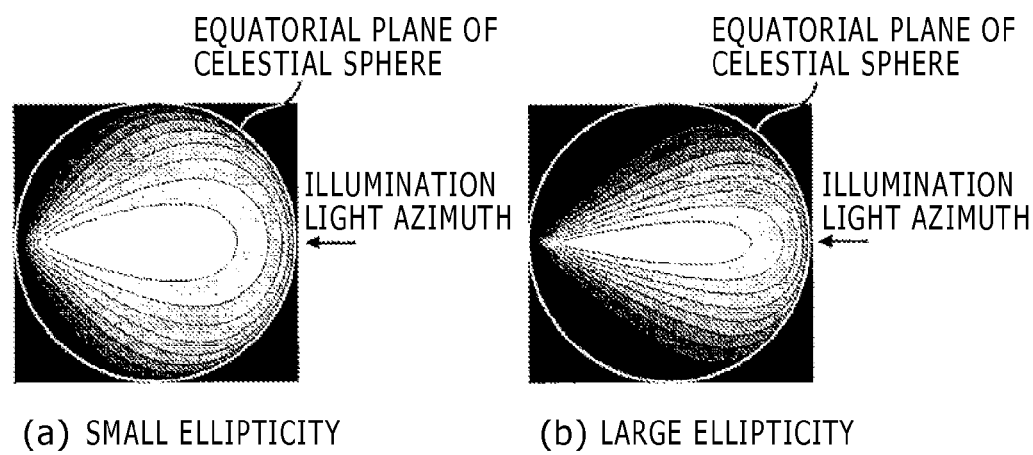
FIG. 8 is a diagram explaining a relationship between ellipticity of the anisotropy and the scattered light distribution.

FIG. 8 shows a relationship between the ellipticity of the anisotropy and the scattered light distribution. Here, the chief axis of the anisotropy is supposed to be in parallel to the azimuth of the illumination light. When the ellipticity is large (a state of FIG. 8 (b)), it turns out that a range where the scattered light is strong is shifted toward the plane of incidence as compared with the case where the ellipticity is small (a state of FIG. 8 (a)). That is, when the ellipticity of the anisotropy varies, the scattered light distribution varies largely in a direction perpendicular to the plane of incidence.

Figure 9:
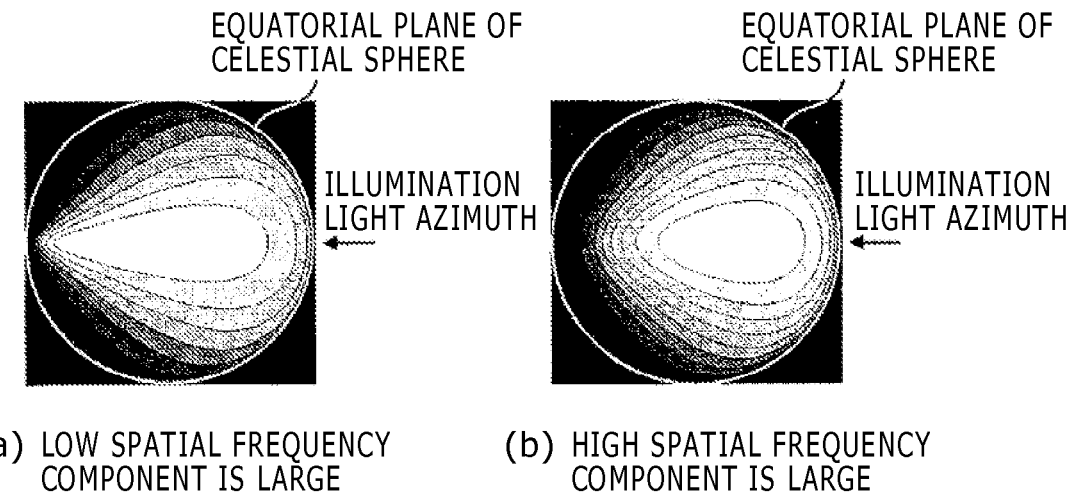
FIG. 9 is a diagram explaining a relationship between a spatial frequency component and the scattered light distribution.

FIG. 9 shows a relationship between the spatial frequency component of the microroughness and the scattered light distribution. Here, the chief axis of the anisotropy is supposed to be in parallel to the azimuth of the illumination light. When a high spatial frequency component is large (a state of FIG. 9 (b)), it turns out that a range where the scattered light is strong is shifted to the back with respect to a travelling direction of the illumination light as compared with the case where a low spatial frequency component is large (a state of FIG. 9 (a)). That is, when a spatial frequency characteristic of the microroughness varies, the scattered light distribution varies largely in a direction parallel to the plane of incidence.

Summarizing explanations of FIG. 7 to FIG. 9, they can be expressed as follows:

(1) When the chief axis direction of the anisotropy varies, the scattered light distribution varies largely in a direction perpendicular to the plane of incidence.
(2) When the ellipticity of the anisotropy varies, the scattered light distribution varies largely in a direction perpendicular to the plane of incidence.
(3) When the spatial frequency characteristic of the microroughness varies, the scattered light distribution varies largely in a direction parallel to the plane of incidence.

That is, when attention is paid to the change in the scattered light distribution relative to the plane of incidence, information about the microroughness having anisotropy will be acquired.

Figure 10:
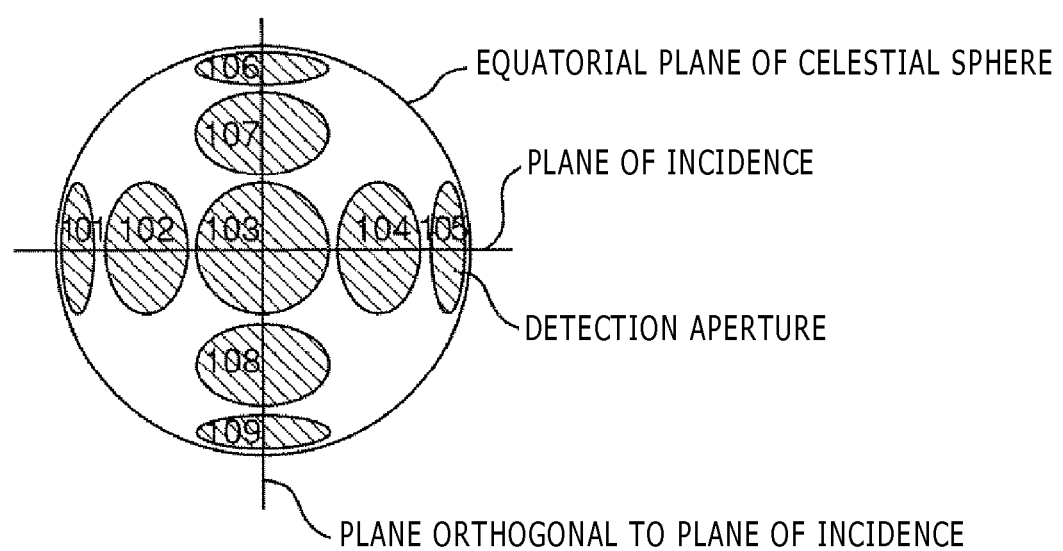
FIG. 10 is a diagram showing an arrangement of the detection optical system in the first embodiment of a surface inspection device according to the present invention.

In order to detect the variation of the scattered light distribution by a difference of the anisotropy and a difference of the spatial frequency characteristic like these, respective detection apertures 101 to 109 of the detection optical systems 51 to 59 of this embodiment are arranged as shown in FIG. 10 (the apertures on the celestial sphere are displayed being projected onto a plane parallel to the wafer surface). Centers of the respective detection apertures 106 to 109 of the detection optical systems 56 to 59, i.e., optical axes of the detection optical systems lie in a plane perpendicular to the plane of incidence. As another expression, this can also be expressed by that a projection line of a plane perpendicular to the plane of incidence to the wafer surface passes though projection images of the detection apertures 106 to 109 that are projected to the wafer surface. Furthermore, the detection apertures 106 and 109 are supposed to be symmetrical relative to the plane of incidence, and the detection apertures 107 and 108 are supposed to be symmetrical relative to the plane of incidence. Since the scattered light distribution varies largely in a direction perpendicular to the plane of incidence when the chief axis direction or the ellipticity of the anisotropy varies, it is possible to detect the variation of the scattered light distribution sensitively with the above-mentioned arrangement.

On the other hand, the centers of the respective detection apertures 101 to 105 of the detection optical systems 51 to 55, i.e., the optical axes of the detection optical systems lie in the plane of incidence. As another expression, this can also be expressed that the projection line of the plane of incidence to the wafer surface passes though projection images of the detection apertures 101 to 105 projected to the wafer surface. Since when the spatial frequency characteristic varies, the scattered light distribution varies largely in a direction parallel to the plane of incidence, it is possible to detect the variation of the scattered light distribution sensitively by the above-mentioned arrangement.

By arranging the detection optical systems 51 to 59 taking into consideration the information about the anisotropy of the microroughness as described above, it is possible to grasp a variation of the anisotropy and a variation of the spatial frequency characteristic in the 2-D spatial frequency spectrum sensitively. Therefore, the measurement accuracy of the microroughness having anisotropy improves.

Next, computation of the 2-D spatial frequency spectrum of the microroughness having anisotropy (Step 203 of FIG. 2) will be explained in detail. Generally, the 2-D spatial frequency spectrum can be approximately expressed with a function containing some parameters. As a typical example, an anisotropic ABC-type function P(f, θ) will be explained. This function is the ABC-type function $P_0(f)$ known conventionally added with a weight function W(θ) representing the anisotropy. Definitions are shown in formulae (1) to (5).

$$f=(f_X^2+f_Y^2)^{1/2} \quad (1)$$

$$\theta=\tan^{-1}(f_Y/f_X) \quad (2)$$

$$P_0(f)=A/(1+(B\times f)^2)^{c/2} \quad (3)$$

$$W(\theta)=\epsilon/(2-\epsilon)\times\cos(2(\theta-\alpha))+1 \quad (4)$$

$$P(f,\theta)=P_0(f)\times W(\theta) \quad (5)$$

Here, $f_X$ and $f_Y$ are spatial frequencies of the X-direction and Y-direction, respectively. A is related to a power in a low spatial frequency range, B is related to a reciprocal of a cutoff spatial frequency, and C is related to inclination on in a high spatial frequency range. Moreover, α is an angle that the chief axis of the anisotropy makes with the spatial frequency axis of the X-direction and ε is the ellipticity.

FIG. 11 shows one example of the 2-D spatial frequency spectrum expressed by the anisotropic ABC-type function. The computation of the 2-D spatial frequency spectrum reduces to finding parameters α, ε regarding the anisotropy and parameters A, B, and C regarding the spatial frequency characteristic.

Figure 12:
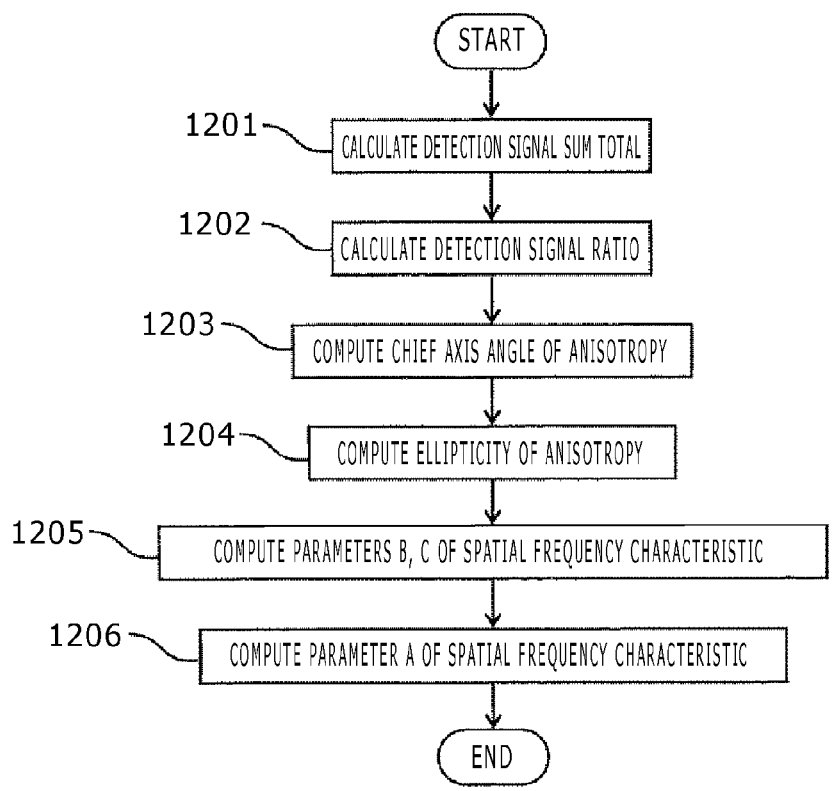
FIG. 12 is a diagram showing a computation flow of the 2-D spatial frequency spectrum expressed with the anisotropic ABC-type function.

FIG. 12 shows a computation flow of the 2-D spatial frequency spectrum expressed by the anisotropic ABC-type function. Here, the chief axis direction of the anisotropy is set fixed to the reference line of the wafer at every measurement position over the wafer. Moreover, the X-direction of a rectangular coordinate system is brought into correspondence with the reference line (argument of 0° of the polar coordinate system). First, after Step 202 of FIG. 2, at each measurement position over the wafer 1, a sum total of all the detection signals of the detectors is calculated (Step 1201).

Next, a ratio of each detection signal and the detection signal sum total, i.e., a detection signal ratio is calculated (Step 1202).

Then, an argument at which the both detection signal ratios of two detectors that are symmetrical relative to the plane of incidence (explaining them in FIG. 10, a combination of the photodetector 66 of the detection optical system 56 and the photodetector 69 of the detection optical system 59, and a combination of the photodetector 67 of the detection optical system 57 and the photodetector 68 of the detection optical system 58) become equal is extracted. The chief axis of the anisotropy is parallel or perpendicular to a direction of the extracted argument (four kinds per 360° rotation of the wafer). Therefore, referring to the library, an argument parallel to the chief axis of the anisotropy is computed. This argument is an angle α that the chief axis of the anisotropy makes with the X-direction (Step 1203).

Next, in an arbitrary argument ϕ, an angle that the chief axis of the anisotropy and the azimuth of the illumination light make is given by ϕ−α. Then, ellipticity ϵ of the anisotropy is computed by comparing the detection signal ratio at the angle ϕ−α with a corresponding library (Step 1204).

Next, the parameters B, C of the spatial frequency characteristic are computed by comparing the detection signal ratio at the angle ϕ−α and the ellipticity ϵ with the corresponding library (Step 1205).

Last, the parameter A is computed by comparing the sum total at the angle ϕ−α, the ellipticity ϵ, and the parameters B, C with the corresponding library (Step 1206).

The computation of the above-mentioned parameters α, ϵ, A, B, and C can be made by numerical calculation such as a least squares method. Thus, since a volume of data is compressible by approximating the 2-D spatial frequency spectrum with a function and expressing it with a small number of parameters, data of the 2-D spatial frequency spectrums at all the measurement positions can be saved.

In the above embodiment, although all the parameters of the anisotropic ABC-type function were computed, there is a parameter that hardly varies even when a state and process conditions of a process apparatus vary depending on a process. In this case, in that process, the parameter whose variation is small may be set to a fixed value (the computation is omitted), and only a parameter whose variation is large may be computed. For example, suppose that the parameters α, ϵ, B, and C hardly vary and the parameter A varies largely as a result of AFM measurement of the test wafer. In this case, the parameters α, ϵ, B, and C may be set to fixed values and only the parameter A may be computed.

Moreover, although in this embodiment, the explanation was given about the anisotropic ABC-type function that was defined by formulae (1) to (5), other suitable functions may be used according to the microroughness of a measurement object.

Next, the computation and the output of the feature quantity of the microroughness will be explained. An operator selects the feature quantity to which attention is paid according to the process using a display device and an input device of the operation system 9. The signal processing system 7 computes the selected feature quantity. Here, the feature quantities include, for example, a chief-axis angle of anisotropy of the 2-D spatial frequency spectrum (angle that the chief axis makes with the reference line 405 of the wafer of FIG. 4), ellipticity of the anisotropy, RMS roughness in a predetermined the 2-D spatial frequency spectrum range, and the cutoff spatial frequency and a peak spatial frequency of the 2-D spatial frequency spectrum, etc. The RMS roughness is acquired by integrating the 2-D spatial frequency spectrum in the spatial frequency range. In this embodiment, since the 2-D spatial frequency spectrum is computed as a continuous function of spatial frequency, the spatial frequency range can be set up arbitrarily.

Figure 13:
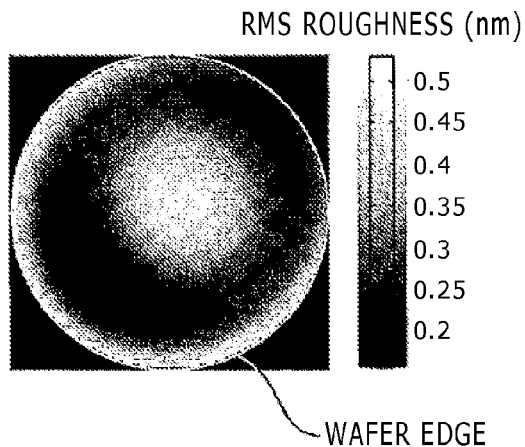
FIG. 13 is a diagram showing one example of a map of RMS roughness in an entire surface of the wafer.

FIG. 13 shows one example of a map of the RMS roughness in the entire surface of the wafer. The map of the RMS roughness proves whether the state and the process conditions of the process apparatus are proper.

Moreover, the cutoff spatial frequency and the peak spatial frequency are computed by analysis of the 2-D spatial frequency spectrum. In this embodiment, since the 2-D spatial frequency spectrum is computed as a continuous function of spatial frequency, they are analyzable with high spatial frequency resolution. The map of the cutoff spatial frequency proves how much the roughness of high spatial frequency exists. Moreover, the map of the peak spatial frequency proves whether the roughness in a specific direction and of a specific spatial frequency like that of the step-terrace structure exists.

Figure 14:
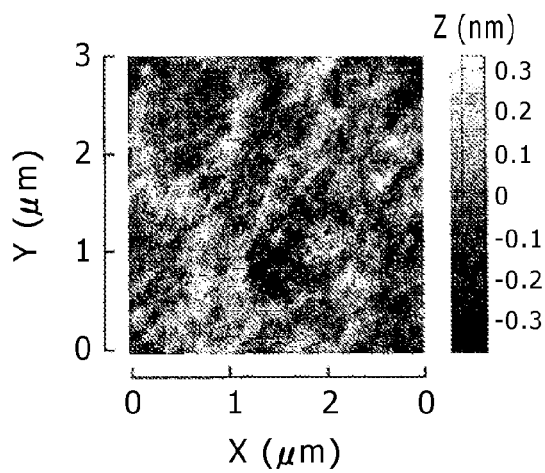
FIG. 14 is a diagram showing one example of an output of a 3-D shape.

Next, computation and an output of a 3-D shape of the microroughness will be explained. The operator specifies a position to which attention should be paid over the wafer referring to the map of the above-mentioned feature quantity. Moreover, the operator specifies a spatial frequency range to which attention should be paid. Using the 2-D spatial frequency spectrum of the position, the signal processing system 7 performs a 2-D inverse Fourier transform in the spatial frequency range to compute coordinates (X, Y, Z) of the 3-D shape. In this embodiment, since the 2-D spatial frequency spectrum is computed as a continuous function of spatial frequency, the spatial frequency range can be set up arbitrarily. The coordinate data is transmitted to the operation system 9, and the 3-D shape at the specified position is outputted. FIG. 14 shows one example of the output of the 3-D shape of the microroughness. By display like this, the operator can recognize the microroughness visually.

Here, in order to perform the 2-D inverse Fourier transform, an amplitude and a phase are required, but phase information is not included in the 2-D spatial frequency spectrum. However, since the phase of the microroughness is random, the phase can be given by generating random numbers. That is, a flow in which the signal processing system 7 acquires the 3-D shape is as follows:

(1) Let a square root of the 2-D spatial frequency spectrum (power) be an amplitude U.
(2) Generate phase δ (in a range of 0 to 2π) with uniform random numbers.
(3) Perform the 2-D inverse Fourier transform of complex amplitude U×(cos δ+i×sin δ).

Incidentally, a bare wafer or a film-coated wafer may be used as the wafer 1. In the case of the film-coated wafer whose film is transparent, microroughness of an interface of the film and the substrate and a thickness of the film can also be measured.

According to this embodiment, for example, by detecting the spatial distribution of the scattered light and computing the 2-D spatial frequency spectrum, it becomes possible to perform high precision measurement of the microroughness having anisotropy.

Second Embodiment

Next, a second embodiment will be explained. The second embodiment is one that expands a detectable spatial frequency range in contrast to the first embodiment.

Figure 15:
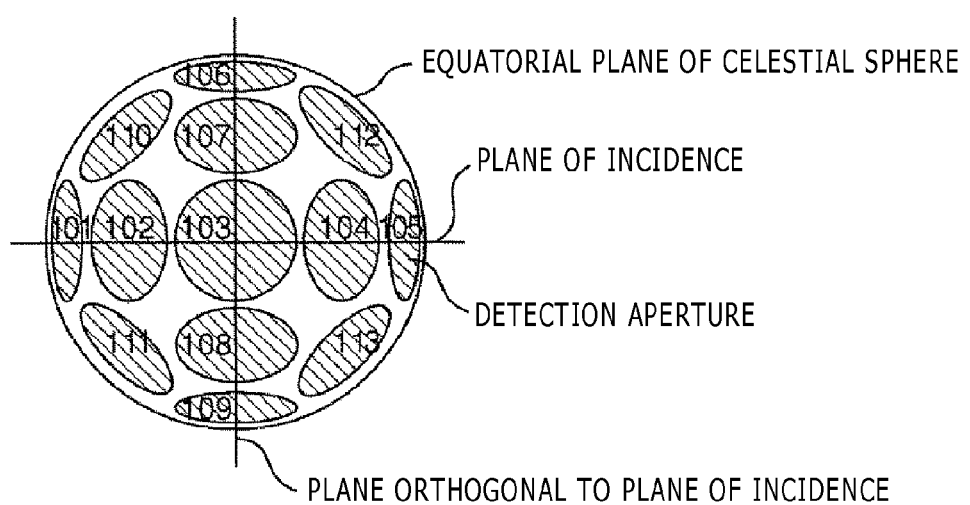
FIG. 15 is a diagram showing an arrangement of a detection optical system in a second embodiment.

FIG. 15 shows an arrangement of detection optical systems (apertures on the celestial sphere are projected onto a plane parallel to the wafer surface). The second embodiment has 13 detection optical systems and 13 photodetectors corresponding to them. That is, detection apertures 110 to 113 are supplemented to the first embodiment. The detection apertures 110 and 111 are configured to be symmetrical relative to the plane of incidence, and the detection apertures 112 and 113 are configured to be symmetrical relative to the plane of incidence.

By the arrangement of the detection optical systems like this, a detectable spatial frequency range can be expanded. As a result, it becomes possible to grasp a variation of the 2-D spatial frequency spectrum sensitively, which improves the measurement accuracy of the microroughness having anisotropy.

Third Embodiment

Next, a third embodiment will be explained. The third embodiment improves the resolution of detectable spatial frequency in contrast to the first embodiment and the second embodiment.

Figure 16:
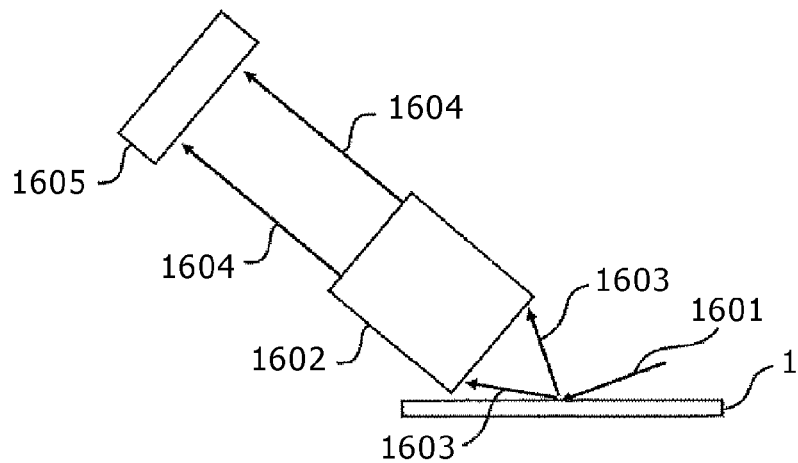
FIG. 16 is a diagram showing a set of a detection optical system and a photodetector in a third embodiment.

FIG. 16 shows the scattered light detection by a set of a detection optical system and a photodetector. A point that illumination light 1601 is irradiated to the wafer 1 is the same as the first embodiment and the second embodiment. In the third embodiment, the detection optical system that was referred to in the first embodiment and the second embodiment is substituted with a Fourier transform optical system 1602. The Fourier transform optical system 1602 collects scattered light 1603 diverging from the wafer, and emits parallel light 1604. Then, the parallel light is detected by a 2-D sensor 1605. As the 2-D sensor, a charge-coupled device (CCD), a time delay integral sensor (TDI), a multi-pixel photon counter, an avalanche photodiode array, etc. can be used. After the scattered light is detected by the 2-D sensor, the same signal processing as the cases of the first and second embodiments is performed.

In the third embodiment, since even with the set of the detection optical system and the photodetector, the spatial distribution of the scattered light can be detected, it is possible to further improve the spatial frequency resolution of the surface measurement device. As a result, it becomes possible to grasp a variation of the 2-D spatial frequency spectrum sensitively, and the measurement accuracy of the microroughness having anisotropy improves.

As explained in detail in the above first to third embodiments, with the surface measurement device of the present invention, it is possible to measure the microroughness of the wafer surface in a semiconductor manufacturing process with high precision, and to manage the state and the process conditions of the process apparatus properly.

Moreover, the surface measurement device of the present invention is widely applicable also to measurement of microroughness of surfaces such as of a magnetic storage medium.

Fourth Embodiment

As another embodiment of the present invention, a defect inspection device of the wafer surface in the semiconductor device manufacture will be explained.

A configuration of the surface inspection device is fundamentally the same as that of the surface measurement device shown in FIG. 1. Hereafter, explanations of common portions are omitted, and only the signal processing system 7 will be explained.

Figure 17:
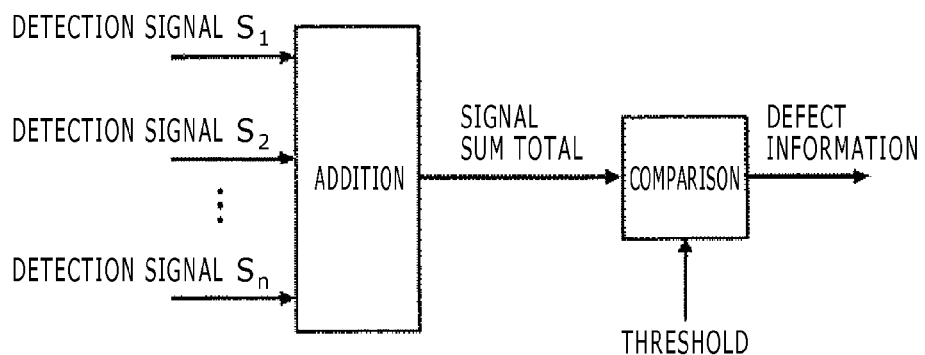
FIG. 17 is a diagram showing signal processing of a conventional surface inspection device.
Figure 18:
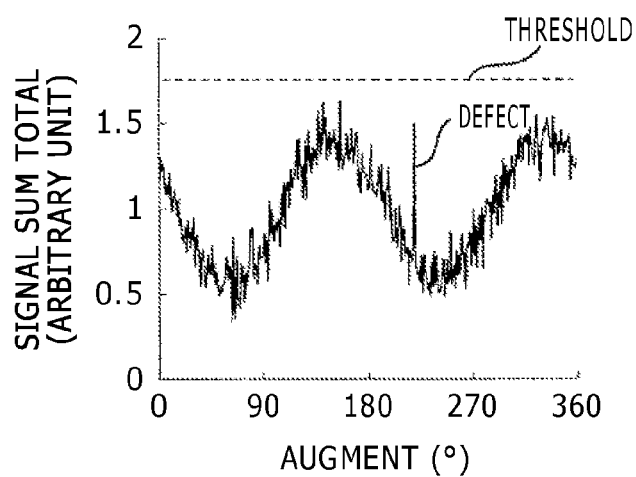
FIG. 18 is a diagram explaining a relationship between an argument of an inspection position and a signal sum total in the conventional surface inspection device.

FIG. 17 shows signal processing of defect detection in a conventional surface inspection device. The detection signals $S_1, S_2, \ldots, S_n$ acquired by multiple detection optical systems are added to acquire the signal sum total. On the other hand, a suitable threshold is set up by referring to a background signal from the microroughness. Then, the signal sum total and the threshold are compared, and when the signal sum total is larger than the threshold, it is determined that there is a defect at an inspection position. However, when the microroughness has anisotropy, the scattered light distribution varies according to the angle that the chief axis direction of the anisotropy and the azimuth of the illumination light make as shown in FIG. 7. For this reason, even when the microroughness is the same in the wafer surface, the background signal will vary with the rotation of the wafer. FIG. 18 shows a relationship between an argument of the inspection position and the signal sum total in the rotation of the wafer 1. In this case, since the threshold needs to be set larger than a maximum of the background signal, a defect is undetectable.

Figure 19:
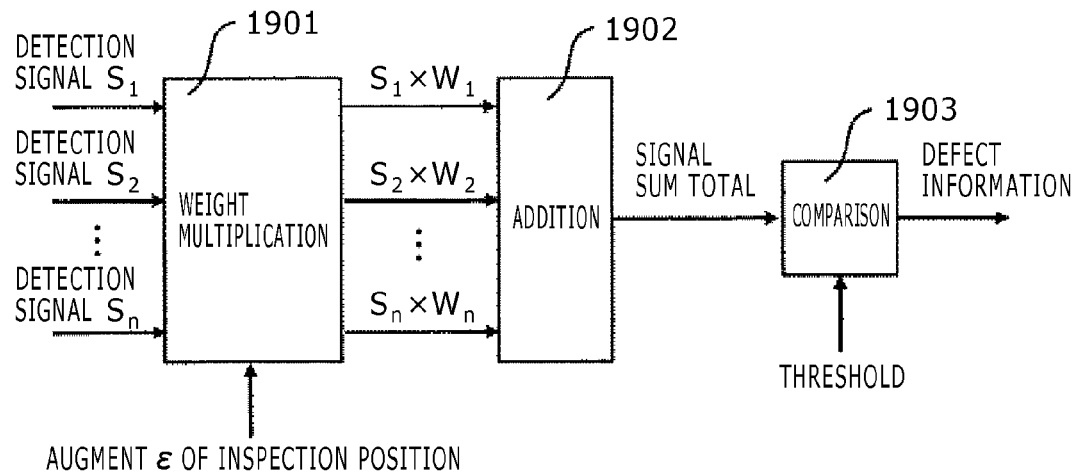
FIG. 19 is a diagram showing signal processing in a fourth embodiment.

FIG. 19 shows the signal processing of defect detection that the signal processing system 7 of the surface inspection device of this embodiment performs. In a weight multiplication part 1901 in the signal processing system 7, the detection signals $S_1, S_2, \ldots, S_n$ acquired by multiple detection optical systems are multiplied by the weight coefficients $W_1, W_2, \ldots, W_n$, respectively. The weight coefficients are functions of the argument of the inspection position, and are set up so as to negate a variation of the background signal accompanying the rotation of the wafer 1. In an adder part 1902, the results of the weight multiplication part 1901 are added to acquire the signal sum total. In a comparison part 1903, the signal sum total and the threshold are compared. When the signal sum total is larger than the threshold, it is recognized that the signal sum total indicates a defect. The comparison part 1903 stores a position of a defect being associated with polar coordinates in the wafer 1.

Figure 20:
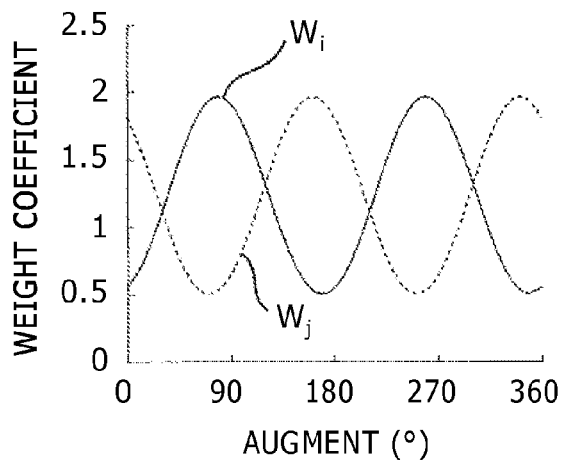
FIG. 20 is a diagram showing one example of a weight coefficient of a detection signal in the fourth embodiment.

FIG. 20 shows one example of weight coefficients $W_i$, $W_j$ to detection signals $S_i$, $S_j$ by two detection optical systems that are symmetrical relative to the plane of incidence. Thus, the weight coefficient differs for every detection signal. Then, the signal sum total is acquired by adding $S_1 \times W_1$, $S_2 \times W_2, \ldots, S_n \times W_n$.

Figure 21:
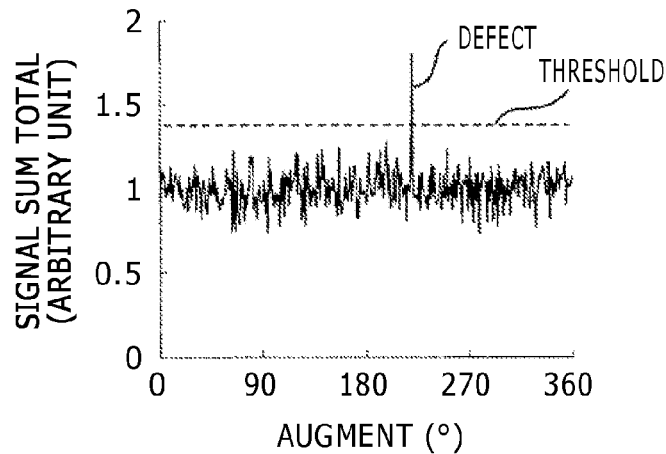
FIG. 21 is a diagram explaining a relationship between an argument of the inspection position and the signal sum total in the fourth embodiment.

FIG. 21 shows a relationship between the argument of the inspection position and the signal sum total in the rotation of the wafer 1 regarding the surface inspection device of this embodiment. Since the maximum of the background signal is small compared with that of the conventional surface inspection device, a threshold can be set small. On the other hand, the defect signal is the same as in the conventional surface inspection device. As a result, the defect overlooked by the conventional surface inspection device can be detected.

Figure 22:
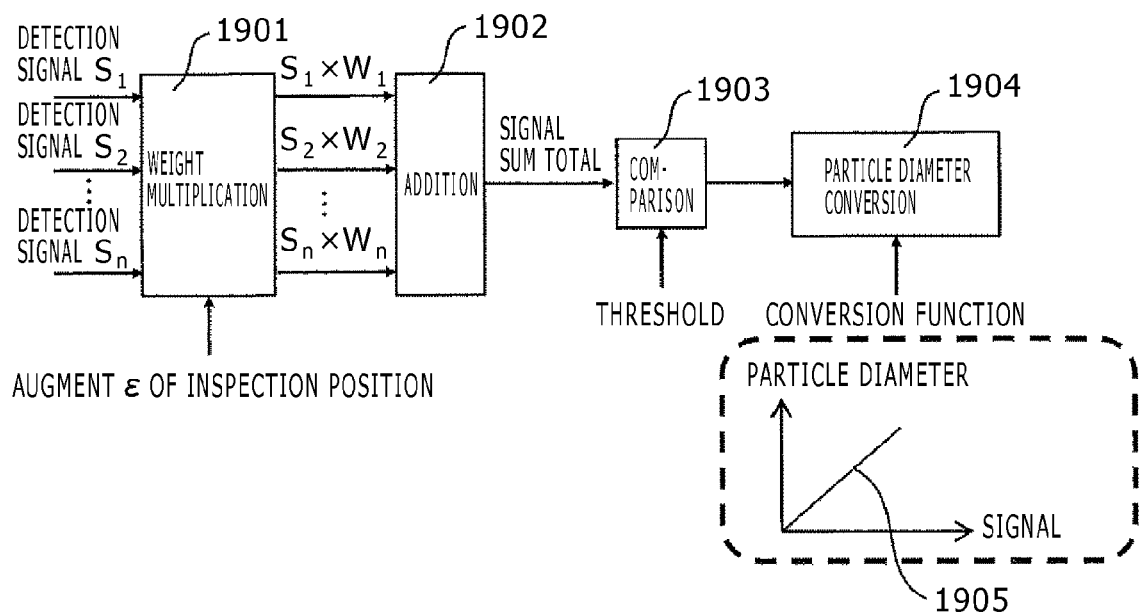
FIG. 22 is a diagram explaining particle diameter conversion in the fourth embodiment.

Furthermore, it is also possible to provide a particle diameter analysis part 1904 in a latter stage of the comparator 1903 as shown in FIG. 22 in the surface inspection device of this embodiment. The particle diameter analysis part 1904 acquires a particle diameter of the defect by comparing the signal sum total of the position judged to be the defect and a conversion function 1905. Incidentally, this conversion function is acquired by inspecting a wafer, for example, over which standard particles such as polystyrene latex spheres whose size is known are coated with the surface inspection device of this embodiment. Incidentally, as long as a function can convert the particle diameter, the conversion function described above may be replaced with that function.

According to this embodiment, it becomes possible to achieve high-sensitivity detection of the defect over the surface with the microroughness having anisotropy, for example, by multiplying a detection signal by a weight according to the argument of the inspection position over the wafer. Moreover, also in defects over the surface with the microroughness having anisotropy, it is possible to acquire its particle diameter more correctly.

As explained in detail in the above fourth embodiment, with the surface inspection device of the present invention, it is possible to detect a defect of the wafer surface in the semiconductor manufacturing process with high sensitivity, and to manage the state and the process conditions of the process apparatus properly. Moreover, the surface inspection device of the present invention is widely applicable also to defect inspection of a surface of a magnetic storage medium etc.

LIST OF REFERENCE SIGNS

1 Wafer
2 Stage

3 Light source
4 Illumination optical system
7 Signal processing system
8 Control system
9 Operation system
51, 52 Detection optical system
61, 62 Photodetector

The invention claimed is:

1. A surface measurement device, comprising:
an illumination optical system for illuminating light on a sample;
a plurality of detection optical systems for detecting scattered light from the sample; and
a signal processing system for acquiring a continuous 2-D spatial frequency spectrum of the sample using detection signals of the detection optical systems and a library,
wherein the 2-D spatial frequency spectrum is defined by two intersecting spatial frequency axes,
wherein the library records a relationship between the 2-D spatial frequency spectrum and the detection signal about known surface roughness,
wherein the processing system acquires a feature quantity about microroughness of the sample,
wherein the feature quantity includes at least one of the following
(a) information about anisotropy of the 2-D spatial frequency spectrum;
(b) a cutoff spatial frequency of the 2-D spatial frequency spectrum; and
(c) a peak spatial frequency of the 2-D spatial frequency spectrum.

2. The surface measurement device according to claim 1, wherein the information about the anisotropy of the 2-D frequency spectrum includes a chief-axis angle of the anisotropy of the 2-D spatial frequency spectrum.

3. The surface measurement device according to claim 1, wherein the information about the anisotropy of the 2-D frequency spectrum includes ellipticity of the anisotropy.

4. The surface measurement device according to claim 1, wherein the feature quantity includes RMS roughness in a predetermined 2-D spatial frequency range.

5. The surface measurement device according to claim 1, wherein optical axes of the at least two detection optical systems lie in a plane substantially perpendicular to the plane of incidence of the sample, and
wherein their apertures are symmetrical relative to the plane of incidence.

6. The surface measurement device according to claim 1, wherein the detection optical systems include Fourier transform optical systems.

7. The surface measurement device according to claim 1, wherein the signal processing system acquires at least one among a chief-axis angle of the anisotropy of the 2-D spatial frequency spectrum, ellipticity of anisotropy, mean square root (RMS) roughness in a predetermined 2-D spatial frequency range, a cutoff spatial frequency of the 2-D spatial frequency spectrum, a peak spatial frequency, and a thickness of a film that forms a sample surface.

8. A surface measurement device, comprising:
an illumination optical system for illuminating light on a sample;
a plurality of detection optical systems for detecting scattered light from the sample; and
a signal processing system for acquiring a continuous 2-D spatial frequency spectrum of the sample using detection signals of the detection optical systems and a library,
wherein the 2-D spatial frequency spectrum is defined by two intersecting spatial frequency axes,
wherein the library records a relationship between the 2-D spatial frequency spectrum and the detection signal about known surface roughness,
wherein the signal processing system acquires a feature quantity about microroughness of the sample,
wherein the detection optical systems include a Fourier transform optical system,
wherein the signal processing system performs a step of multiplying signals from the detection optical systems by coefficients, respectively, and a step of detecting a defect over the sample using the signals to which the coefficients are multiplied, and
wherein the coefficients are set up so that a variation of a background signal accompanying rotation of the sample may be negated.

9. The surface measurement device according to claim 8, wherein the signal processing system acquires a size of the defect.

10. A surface measurement device, comprising:
an illumination optical system for illuminating light on a sample;
a plurality of detection optical systems for detecting scattered light from the sample; and
a signal processing system for acquiring a continuous 2-D spatial frequency spectrum of the sample using detection signals of the detection optical systems and a library,
where in the 2-D spatial frequency spectrum is defined by two intersecting spatial frequency axes,
wherein the signal processing system acquires ratios of of respective detection signals of the detection optical systems and the sum of the detection signals and acquires the 2-D spatial frequency spectrum using the detection signal sum total, the detection signal ratios, and the library.

11. A surface measurement device, comprising:
an illumination optical system for illuminating light on a sample;
a plurality of detection optical systems for detecting scattered light from the sample; and
a signal processing system for acquiring a continuous 2-D spatial frequency spectrum of the sample using detection signals of the detection optical systems and a library,
wherein the 2-D spatial frequency spectrum is defined by two intersecting spatial frequency axes,
wherein the signal processing system performs a 2-D inverse Fourier transform on the 2-D spatial frequency spectrum, and
wherein the signal processing system performs the 2-D inverse Fourier transform using random numbers.

12. A surface measurement device, comprising:
an illumination optical system for illuminating light on a sample;
a plurality of detection optical systems for detecting scattered light from the sample; and
a signal processing system for acquiring a continuous 2-D spatial frequency spectrum of the sample using detection signals of the detection optical systems and a library, wherein the 2-D spatial frequency spectrum is defined by two intersecting spatial frequency axes, wherein the signal processing system performs a step of multiplying respective signals of the detection optical systems by coefficients and a step of detecting a defect over the sample using the signals to which the coefficients are multiplied, and wherein the coefficients are set up so that a variation of a background signal accompanying rotation of the sample may be negated.

13. The surface measurement device according to claim 12, wherein the signal processing system acquires a size of the defect.

* * * * *